United States Patent
Chiou et al.

(10) Patent No.: US 6,866,825 B2
(45) Date of Patent: Mar. 15, 2005

(54) MICRO-DISPENSER FOR BIOCHEMICAL ANALYSIS

(75) Inventors: Chung-Fan Chiou, Hsinchu (TW); Ying-Chi Chen, Hsinchu Hsien (TW); Shyh-Haur Su, Hsinchu (TW); Chih-Ping Lu, Yi-Lan (TW); Ching-Yi Mao, Kaohsiung Hsien (TW); Je-Ping Hu, Taipei Hsien (TW)

(73) Assignee: Industrial Technology Research Institute, Hsinchu (TW)

( * ) Notice: Subject to any disclaimer, the term of this patent is extended or adjusted under 35 U.S.C. 154(b) by 472 days.

(21) Appl. No.: 10/021,690

(22) Filed: Nov. 5, 2001

(65) Prior Publication Data

US 2003/0086828 A1 May 8, 2003

(51) Int. Cl.[7] .............................. G01D 15/16; B01L 3/00
(52) U.S. Cl. ...................... 422/100; 422/63; 436/180; 347/6
(58) Field of Search ................... 422/99–104; 347/102; 436/180; 73/863.32

(56) References Cited

U.S. PATENT DOCUMENTS

| | | | | |
|---|---|---|---|---|
| 4,472,357 A | * | 9/1984 | Levy et al. | 422/102 |
| 4,698,644 A | * | 10/1987 | Drago et al. | 347/40 |
| 5,525,304 A | * | 6/1996 | Matsson et al. | 422/104 |
| 6,001,309 A | | 12/1999 | Gamble et al. | |
| 6,110,426 A | | 8/2000 | Shalon et al. | |

FOREIGN PATENT DOCUMENTS

| JP | 2000166535 A1 | 12/1998 |
|---|---|---|
| JP | 2001232245 A1 | 2/2000 |

* cited by examiner

*Primary Examiner*—Jill Warden
*Assistant Examiner*—Jyoti Nagpaul
(74) *Attorney, Agent, or Firm*—Darby & Darby

(57) ABSTRACT

A micro-dispenser for dispensing predetermined amounts of fluids under the control of a controller. The micro-dispenser comprises a base and a high-density array of tube assemblies. The base, having a plurality of holes, is electrically connected to the controller. The tube assemblies, pre-filled with predetermined fluids, are detachably disposed in the holes and separately electrically connected to the base. The tube assemblies dispense the fluids through the base under the control of the controller. The tube assemblies are replaceable.

20 Claims, 8 Drawing Sheets

MICRO-DISPENSER FOR BIOCHEMICAL ANALYSIS

BACKGROUND OF THE INVENTION

1. Field of the Invention

The invention relates to a micro-dispenser for a biological analysis; in particular, the invention relates to a micro-dispenser with replaceable capillary tubes arranged in a high-density array.

2. Description of the Related Art

Reactions between biological molecules exhibit an extremely high degree of specificity. It is this specificity that provides a living cell with the ability to carry out thousands of chemical reactions simultaneously in the same vessel. In general, this specificity arises from the fit between two molecules having very complex surface topologies.

Systems for medical diagnosis often involve a bank of tests in which each test involves the measurement of the binding of one mobile component to a corresponding immobilized component. To provide inexpensive test kits, systems involving a matrix of immobilized spots have been suggested. Each spot includes the immobilized component of a two-component test. The fluid to be tested is typically brought into contact with the matrix.

The matrix is typically constructed by dispensing small quantities of the immobilized component onto a substrate such as glass that has been chemically modified to bind the immobilized component. The amount of material in each spot is relatively small; however, the number of spots may be quite large. Hence, the generation of such an assay plate requires a reliable micro-dispenser that can place the individual spots at predetermined locations with a high degree of precision.

In FIG. 1a and FIG. 1b, a conventional dispenser disclosed in U.S. Pat. No. 6,001,309 is shown. The device 10 has an outer housing 12 that encompasses the capillary assembly. The housing 12 has an opening 14 through which the capillary 16 extends. At the top of the housing is gasket 20. Also shown is the cover 22 employed during cleaning and filling of the device 10. Included in the cover 22 is first conduit 24 for cleaning solvent addition when the system needs to be evacuated or pressurized; second conduit 28 for connecting to a vacuum source; and third conduit 32 for introducing gas pressure. Cover 22 is adjacent to a thread tube 42 that can serve to lock the capillary casing 50 in the housing 12. The threaded tube 42 has a conical receptacle 46 for receiving the sample. After cleaning, the cover 22 is removed exposing the conical receptacle 46, which is then available for receiving a sample. The conical receptacle 46 has a port 48 which meets the capillary, whereby the sample can touch the capillary 16 and by surface tension the sample can move the length of the capillary 16 to fill the capillary. Threaded casing 50 has a notch that extends downward through threaded casing 50 to receive wires 54 for activating the transducer 56. The piezoelectric transducer 56 is proximal to the orifice 60. The walls of the capillary 16 are quite thin, so that they can move with the expansion and contraction of the transducer 56.

FIG. 2 is a schematic flow representation of a system for producing arrays according to U.S. Pat. No. 6,001,309. In FIG. 2, a storage subsystem 300 is shown as an array of racks. Each bin in the rack contains an array of storage well plates 302. A master controller 304 controls the system. Under computer signal, one or more plates 302 are conveyed from the storage area 300 to the next station 306. At the station 306 a robotic arm 308 is under the control of subsystem controller 309. The robotic arm 308 using micropipette tips 310 transfers microliter quantities of liquid from the plate 302 to one or more appropriate jet 312 located at a maintenance and fill station under the control of subsystem controller 315. For reusable jetting devices, the maintenance and fill station has maintenance caps 316. A holder 318 positions the jetting device 312 on a translation bar 320, thereby the jetting device 312 is moved to the test station 322 under the control of subsystem controller 323. If the jetting device 312 passes the test station, it is then moved by means of the translation bar 320 to the jetting position 334 and positioned over the substrate 336 by means of the translation bar 320 and the holder 318. The jetting dispenser is now in position to begin jetting drops to create the array.

Referring to FIG. 3, another conventional dispensing device disclosed in U.S. Pat. No. 6,110,426 is shown. The dispensing device 110 generally includes a reagent dispenser 112 having a capillary channel 114 adapted to hold a quantity of the reagent solution 116. The channel is formed by a pair of members 112a, 112b which are converged at a tip region 118 at the lower end of the channel. At the tip 118, aqueous solution in the channel forms meniscus 120 as shown in FIG. 4a. With the dispenser so positioned, solenoid 122 is activated to draw a piston 124, causing connecting member 126 to move the tip 118 rapidly toward and away from the surface 131 of the substrate 130, making momentary contact with the surface 131. In effect, the tip 118 of the dispenser 112 is tapped against the substrate surface 131. The tapping movement of tip 118 against the surface 131 acts to break the liquid meniscus 120 in the tip channel 114, bringing the liquid in the tip 118 into contact with substrate surface 131. This, in turn, produces a flowing of the liquid into the capillary space between the tip 118 and the surface 131, acting to draw liquid out of the dispenser channel 114, as seen in FIG. 4b. FIG. 4c shows the flow of fluid from the tip 118 onto the substrate surface 131. The figure illustrates that liquid continues to flow from the dispenser 112 onto the substrate surface 131 until it forms a liquid bead 132.

The dispenser must also operate without clogging over a large number of samples. In addition, the dispenser must be able to change samples quickly, as each spot in the matrix requires a different immobilized component.

The dispenser disclosed in U.S. Pat. No. 6,001,309, is reusable; therefore, it must be cleaned and refilled so that the problem of the counter-contamination easily occurs. Furthermore, due to the maintenance time, the whole operation of such a system is troublesome and inconvenient, and the cost is increased.

Similarly, the dispenser disclosed in U.S. Pat. No. 6,110,426 is contact type so that the problem of the counter-contamination also occurs easily.

SUMMARY OF THE INVENTION

In order to address the disadvantages of the aforementioned dispenser, the invention provides a micro-dispenser with replaceable capillary tubes arranged in a high-density array.

Another purpose of the invention is to provide a micro-dispenser that can avoid the problem of counter-contamination.

Accordingly, the invention provides a micro-dispenser for dispensing a predetermined amount of fluids under the control of a controller. The micro-dispenser comprises a base and an array of tube assemblies. The base, having a plurality of holes, is electrically connected to the controller. The tube assemblies, pre-filled with predetermined fluids, are detachably disposed in the holes and separately electrically connected to the base. The tube assemblies deliver the fluids through the base and are replaceable.

In a preferred embodiment, the base is provided with at least one recess formed adjacent to the each hole. Furthermore, the base is provided with at least one first pad disposed in each of the holes. Each of the tube assemblies comprises a receptacle, a capillary tube and a print chip head. The receptacle, having a passage, is provided with at least one protrusion corresponding to recesses in the base and at least one second pad corresponding to the first pads. The second pads abut the first pads when the tube assemblies insert into the holes of the base. The capillary tube, for receiving the fluid, is disposed in the receptacle at one end of the passage. The print chip head, disposed in the receptacle at the other end of the passage, abuts the second pads and communicates with the capillary tube.

Furthermore, each of the tube assemblies is marked with a code indicating the type of fluid contained therein. The base is provided with a first detecting device for detecting the amount of the fluid. Furthermore, each of the tube assemblies is provided with a second detecting device for detecting the amount of the fluid remaining in the capillary tube.

It is understood that the tube assembly could be pulse pressure ink-jet type, bubble jet ink-jet type or slit jet ink-jet type.

Furthermore, this invention provides a dispensing device for a biochemical analysis comprising a controller and at least one micro-dispenser. The micro-dispenser, for dispensing a predetermined amount of reagents to a substrate used in biochemical analysis, is electrically connected to the controller. The micro-dispenser comprises a base and an array of tube assemblies. The base, having a plurality of holes, is electrically connected to the controller. The tube assemblies, pre-filled with predetermined reagents, are detachably disposed in the holes and separately electrically connected to the base. Under the control of the controller, the tube assemblies deliver the reagents through the base when the base faces the substrate. The tube assemblies are replaceable.

BRIEF DESCRIPTION OF THE DRAWINGS

The invention is hereinafter described in detail with reference to the accompanying drawings in which:

FIG. 1b is a cross-sectional view depicting the dispenser as shown in FIG. 1a;

DETAILED DESCRIPTION OF THE INVENTION

Figure 1B:
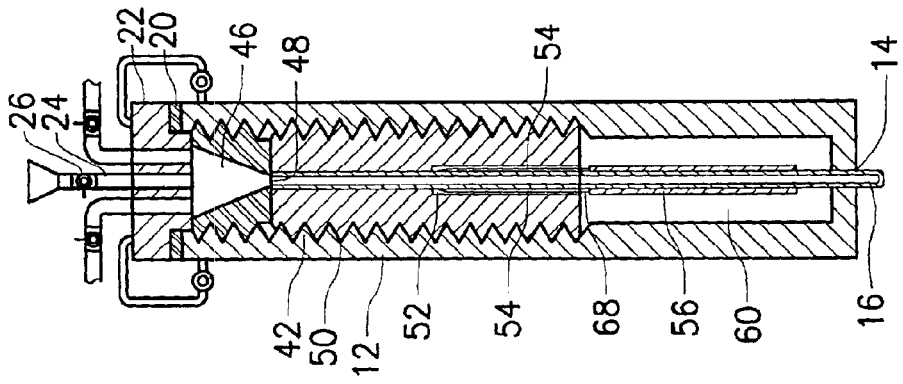
Figure 1A:
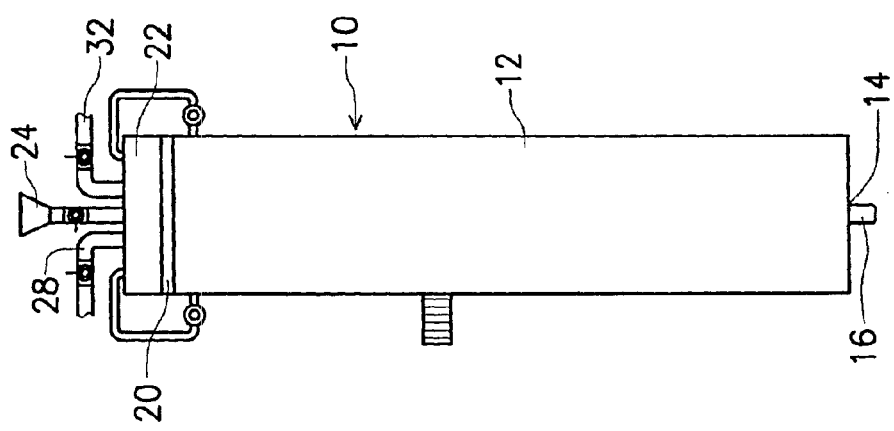
FIG. 1a is a perspective elevational view of a conventional dispenser disclosed in U.S. Pat. No. 6,001,309.
Figure 2:
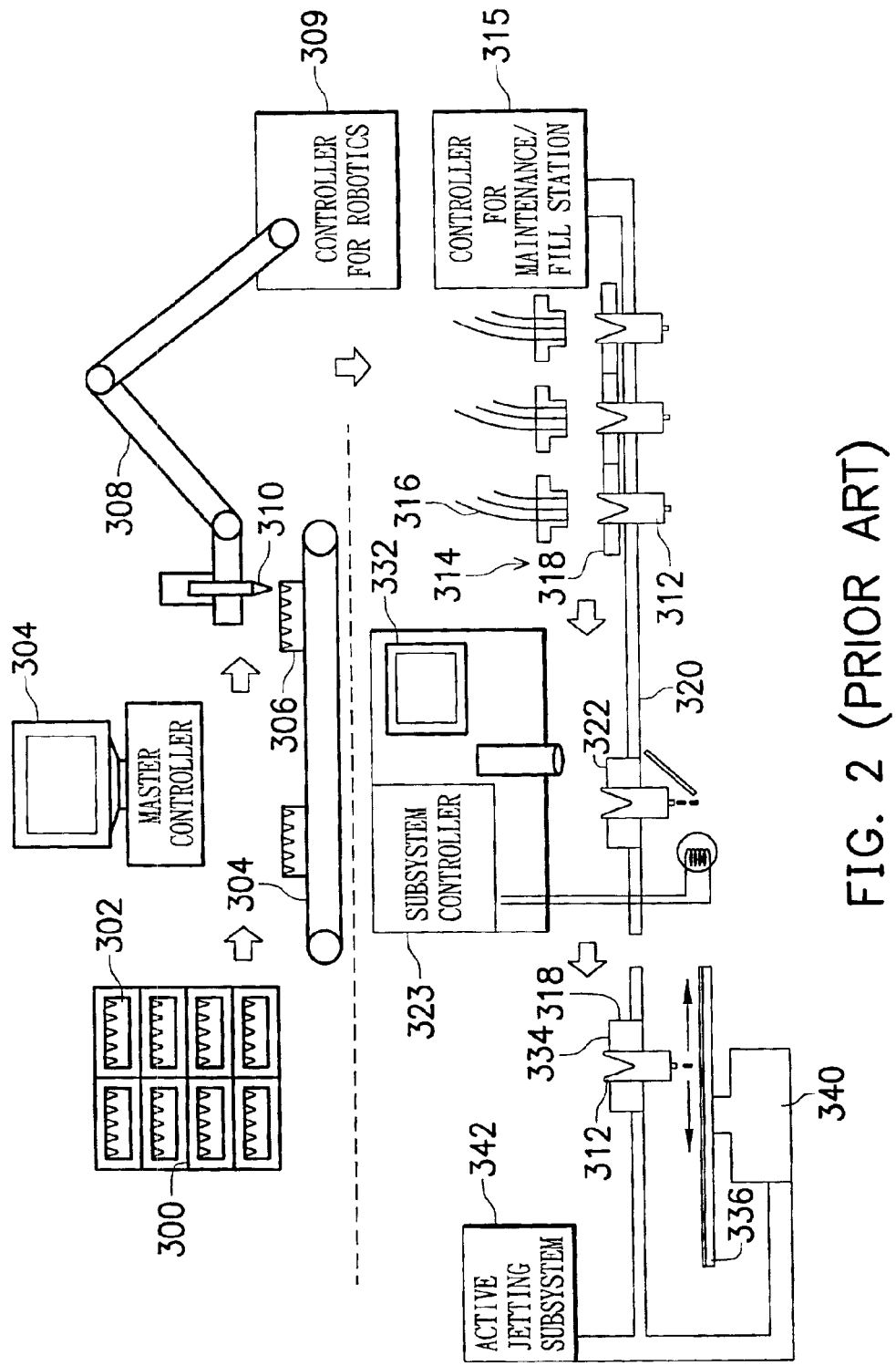
FIG. 2 is a schematic flow representation of a system for producing arrays according to U.S. Pat. No. 6,001,309.
Figure 3:
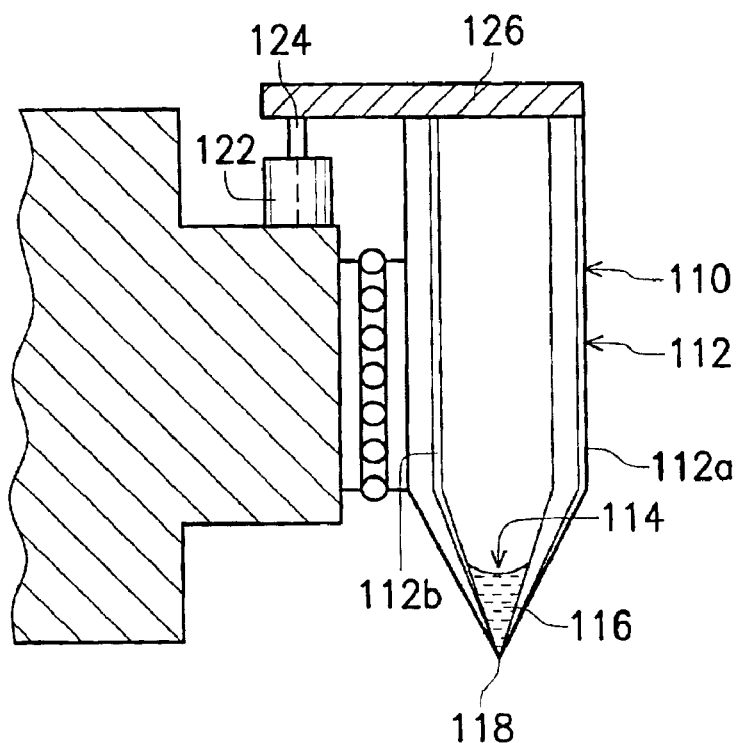
FIG. 3 is a side view depicting another conventional dispensing device disclosed in U.S. Pat. No. 6,110,426.
Figure 4A:
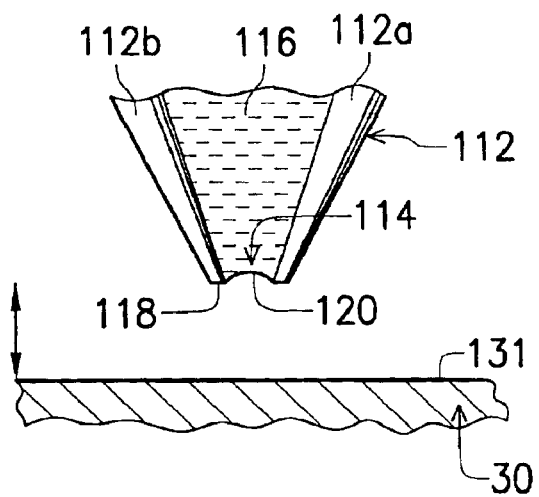
FIGS. 4a–4c illustrates steps in the delivery of a fixed-volume bead on a hydrophobic surface employing the dispenser from FIG. 3.
Figure 4B:
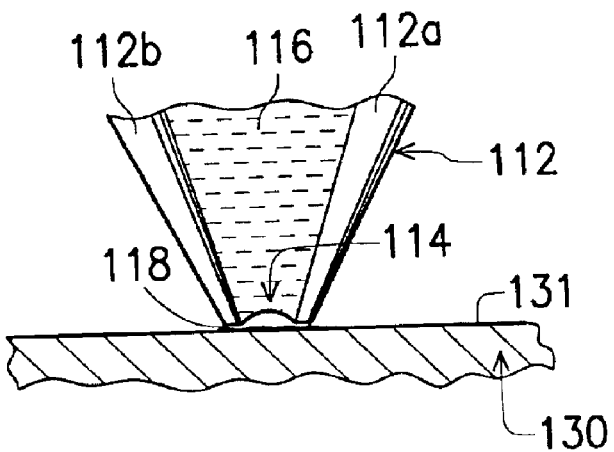
Figure 4C:
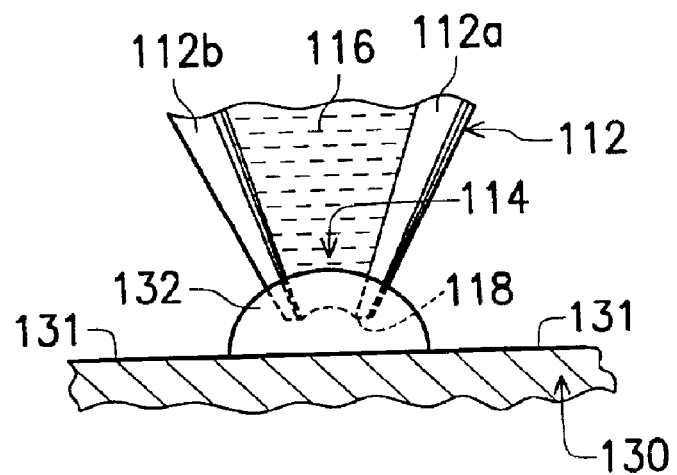
Figure 5A:
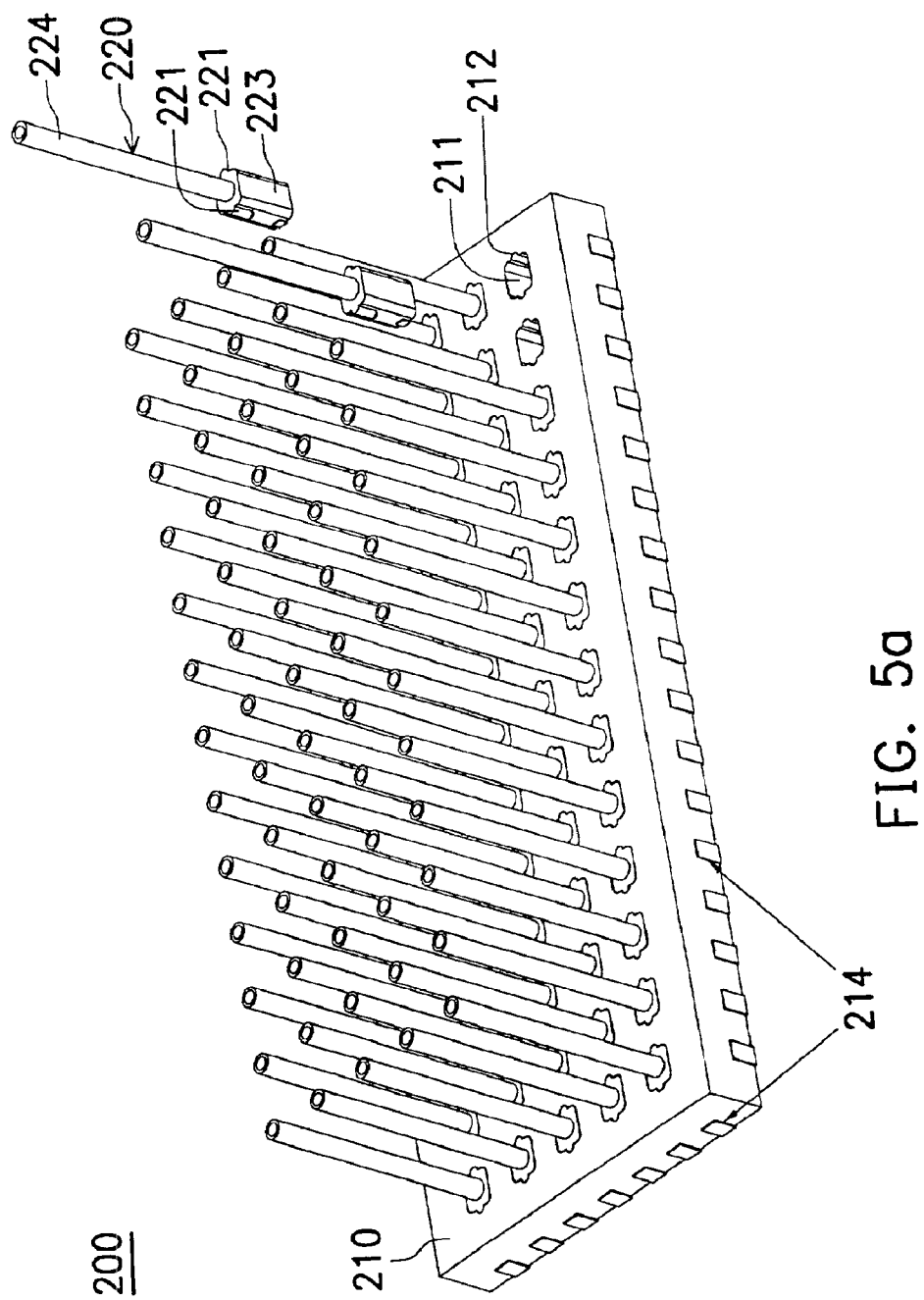
FIG. 5a is a schematic view depicting a micro-dispenser as disclosed in the invention.
Figure 5B:
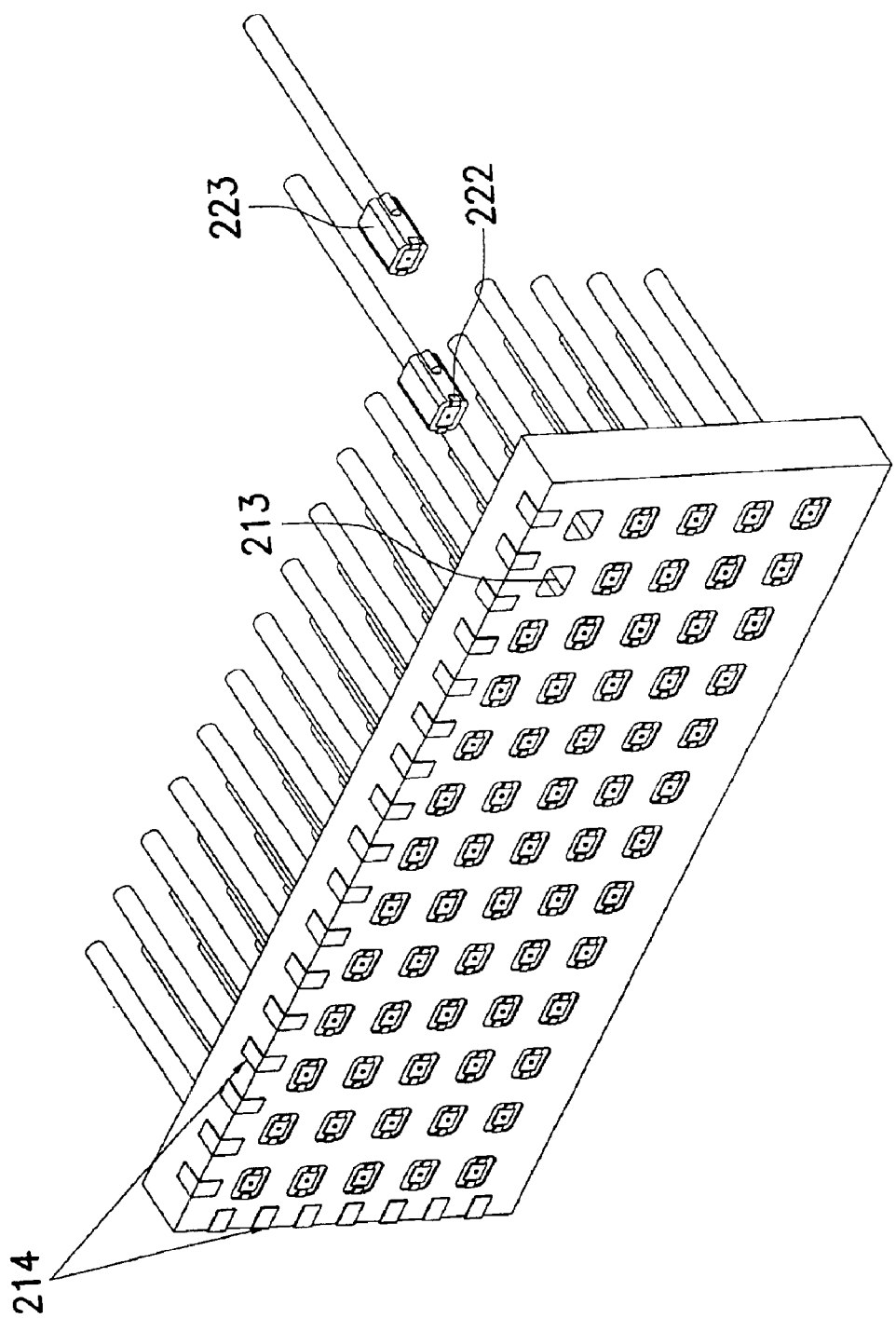
FIG. 5b is a schematic view from a second perspective depicting a micro-dispenser as disclosed in the invention.

Referring to FIG. 5a and FIG. 5b, a micro-dispenser 200 as disclosed in this invention is shown. The micro-dispenser 200 dispenses a predetermined amount of fluids under the control of a controller (not shown in the figure), and comprises a base 210 and an array of tube assemblies 220. The base 210 is electrically connected to the controller 400, and is provided with a plurality of holes 211, a plurality of recesses 212 formed adjacent to the holes 211, a plurality of first pads 213 disposed in each of the holes 211, and a plurality of third pads 214 disposed around the base 210.

Specifically, two recesses 212 are formed at both sides of each hole 211. The third pads 214 are electrically connected to the first pads 213 in a predetermined manner so that the controller 400 can actuate the tube assemblies 220, inserted into the holes 211 of the base 210, via the third pads 214 and the first pads 213.

Figure 6:
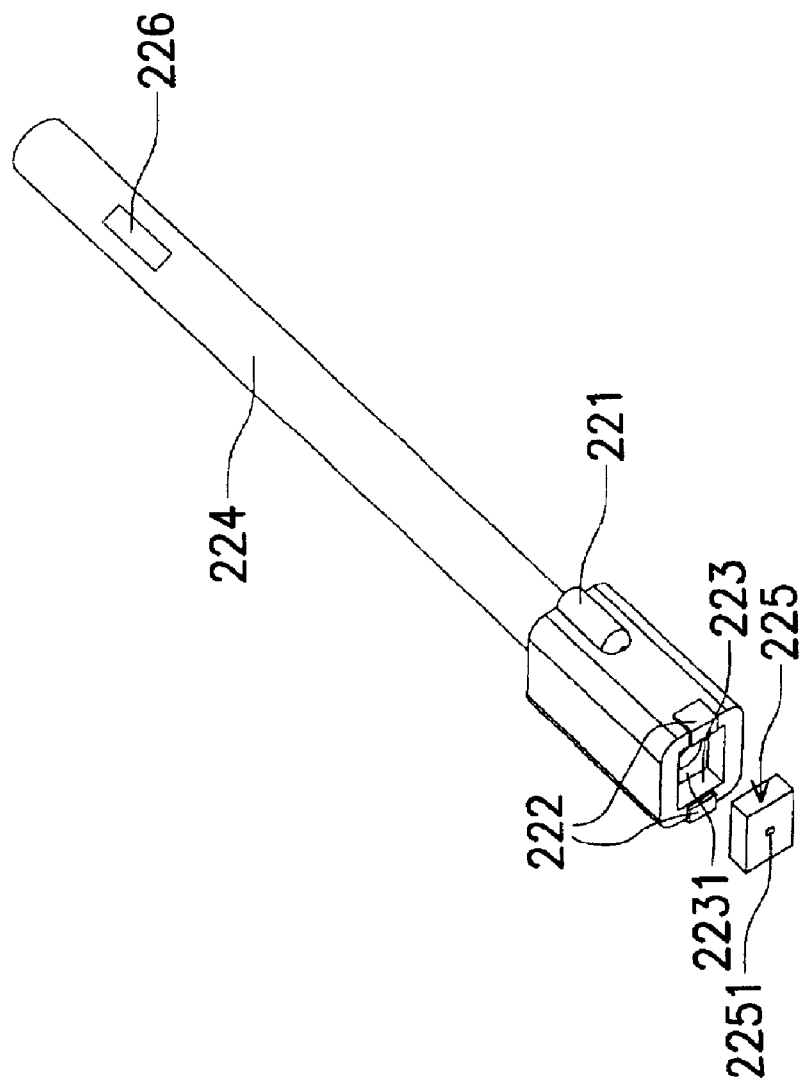
FIG. 6 is a exploded view depicting the tube assembly of the present invention.

The tube assemblies 220, pre-filled with predetermined fluids, are detachably disposed in the holes 211 of the base 210 and electrically connected to the base 210 via the first pads 213. Referring to FIG. 6, each of the tube assemblies 220 is provided with at least one protrusion 221, corresponding to the recesses 212, two second pads 222 corresponding to the first pads 213, a receptacle 223, a capillary tube 224 and a print chip head 225.

Specifically, the protrusions 221 engage with the recesses 212 of the base 210. The second pads 222 abut the first pads 213 when the tube assemblies 220 are inserted into the holes 211 of the base 210. The receptacle 223, having a passage 2231, is provided with the protrusions 221 and the second pads 222. The capillary tube 224, for receiving the fluid, is disposed in the receptacle 223 at one end of the passage 2231. The print chip head 225, disposed in the receptacle 223 at the other end of the passage 2231, abuts the second pads 222 and communicates with the capillary tube 224. The print chip head 225 is provided with a nozzle 2251, communicating with the capillary tube 224, so that the fluid contained in the capillary tube 224 can be dispensed through the nozzle 2251. By this arrangement, the tube assemblies 220 deliver the fluids through the base 210.

It is noted that the fluid, received in the capillary tube 224, is kept by the friction force between the surface property of the capillary tube 224 and the surface tension of the reagents. For increasing the friction force, gel-like or oil-like materials can be added to the filling end of the capillary tube 24 so that the reagents will not leak from the filling end of the capillary tube 24. In addition, the gel-like or oil-like materials will not mix with the reagents.

Furthermore, each of the tube assemblies 220 is provided with a marked with a code 226 indicating the type of fluid contained therein. The base 210 is provided with a first detecting device (not shown) for detecting the amount of the fluid. Furthermore, each of the tube assemblies 220 is provided with a second detecting device (not shown) for detecting the amount of the fluid remaining in the tube.

It is understood that the tube assembly 220 may be pulse pressure ink-jet type or bubble jet ink-jet type or slit jet ink-jet type.

The micro-dispenser of the present invention has the following advantages:

1. By the disengagement of the protrusions 221 and the recesses 212, the tube assemblies 220 are replaceable after the fluid contained in the capillary tube 224 runs out. It is noted that the tube assemblies 220 can also be replaced due to different requirement. In addition, a predetermined amount of the tube assemblies can be preset at one set. Thus, one set of the tube assemblies can be replaced at a time.

2. The fluid is pre-filled in the tube assembly 220 so that the whole tube assembly 220 may be directly replaced when the fluid must be changed.

3. Since no cleaning and refilling are required, the micro-dispenser can avoid the problem of the counter-contamination.

Figure 7:
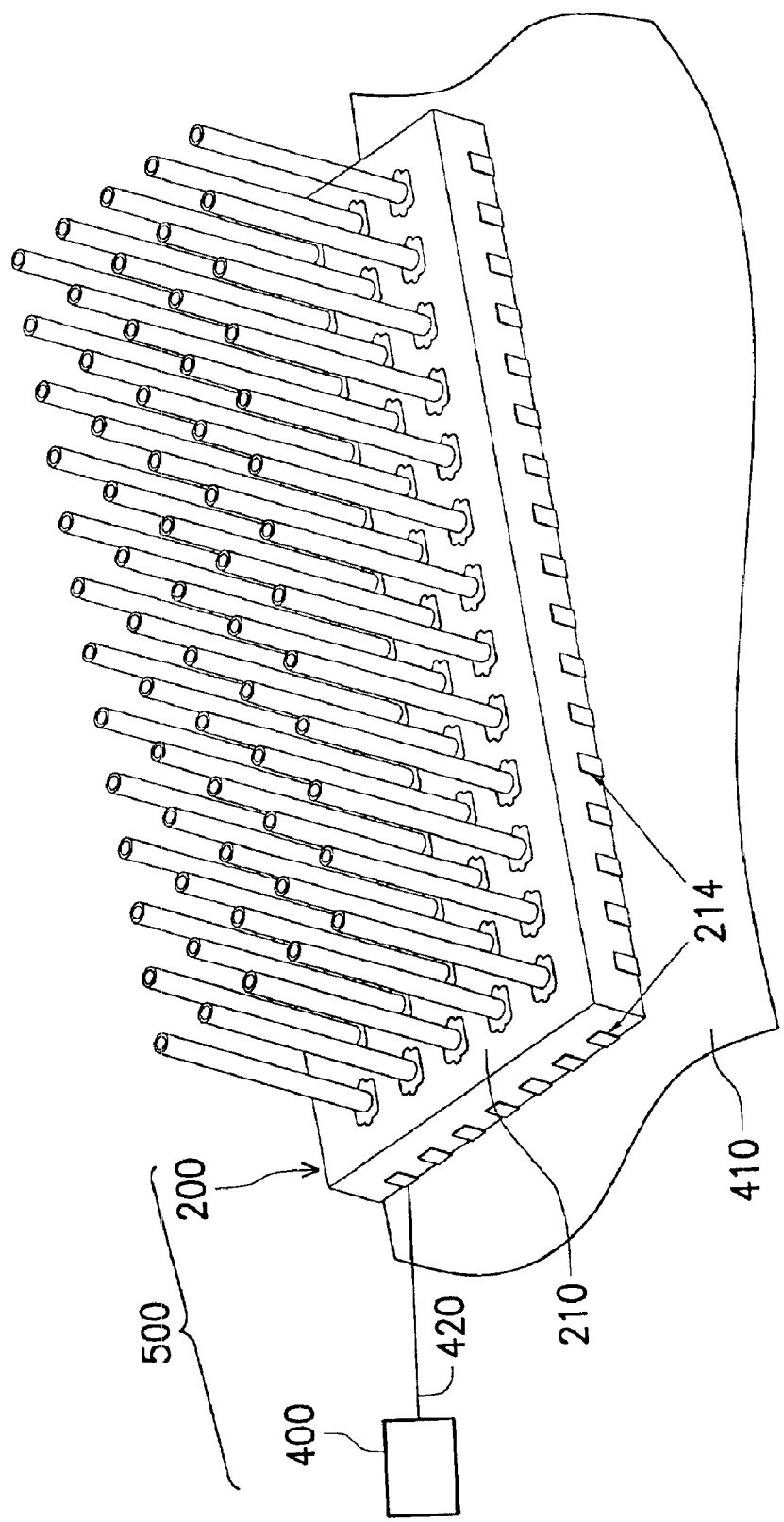
FIG. 7 is a schematic view depicting a dispensing device for a biochemical analysis as disclosed in the invention

Referring to FIG. 7, a dispensing device 500 for a biochemical analysis comprises a controller 400 and at least one micro-dispenser 200. By means of the controller 400, the dispensing device 500 can control one or a plurality of micro-dispensers 200 simultaneously. In biochemical analysis, the micro-dispenser 200 dispenses a predetermined amount of predetermined reagents to a substrate 410. The micro-dispenser 200 is electrically connected to the controller 400 through a wire 420. The tube assembly 220 is pre-filled with predetermined reagents and delivers the reagents through the base 210 when the base faces the substrate 410.

By means of the dispensing device 500 as disclosed in this invention, the assays/kits used in the biochemical analysis can be produced conveniently with high yield.

While the invention has been particularly shown and described with reference to a preferred embodiment, it will be readily appreciated by those of ordinary skill in the art that various changes and modifications may be made without departing from the spirit and scope of the invention. It is intended that the claims be interpreted to cover the disclosed embodiment, those alternatives which have been discussed above, and all equivalents thereto.

What is claimed is:

1. A micro-dispenser for dispensing a predetermined amount of fluids under the control of a controller comprising:
   a base, having a plurality of holes, electrically connected to the controller; and
   an array of tube assemblies, filled with predetermined fluids, detachably disposed in the holes and separately electrically connected to the base, the tube assemblies dispensing the fluids under the control of the controller, wherein the tube assemblies are replaceable;
   wherein each of the tube assemblies further comprises:
   a receptacle having a passage;
   a capillary tube, for retaining the fluid, disposed in the receptacle at one end of the passage; and
   a print chip head, disposed in the receptacle at the other end of the passage, communicating with the capillary tube.

2. The micro-dispenser as claimed in claim 1, wherein the base provided with at least one recess formed adjacent to each hole, and the receptacle of each of the tube assemblies is provided with at least one protrusion corresponding to the at least one recess for engaging with the base.

3. The micro-dispenser as claimed in claim 1, wherein each of the tube assemblies is marked with a code indicating the type of fluid contained therein.

4. The micro-dispenser as claimed in claim 1, wherein the base is provided with a first detecting device for detecting the amount of the fluid.

5. The micro-dispenser as claimed in claim 1, wherein each of the tube assemblies is provided with a second detecting device for detecting the amount of fluid remaining therein.

6. The micro-dispenser as claimed in claim 1, wherein the tube assembly is pulse pressure ink-jet type.

7. The micro-dispenser as claimed in claim 1, wherein the tube assembly is bubble jet ink-jet type.

8. The micro-dispenser as claimed in claim 1, wherein the tube assembly is slit jet ink-jet type.

9. A micro-dispenser for dispensing a predetermined amount of fluids under the control of a controller comprising:
   a base, having a plurality of holes, electrically connected to the controller, wherein the base is provided with at least one first pad disposed in each of the holes separately; and
   an array of tube assemblies, filled with predetermined fluids, detachably disposed in the holes and separately electrically connected to the base, the tube assemblies dispensing the fluids under the control of the controller, wherein the tube assemblies are replaceable;
   wherein each of the tube assemblies further comprises:
   a receptacle having a passage, wherein the receptacle is provided with at least one second pad corresponding to the at least one first pad, and the second pads abut the first pads when the tube assemblies are inserted into the holes of the base;
   a capillary tube, for retaining the fluid, disposed in the receptacle at one end of the passage; and
   a print chip head, disposed in the receptacle at the other end of the passage, communicating with the capillary tube.

10. A micro-dispenser for dispensing a predetermined amount of fluids under the control of a controller comprising:
    a base, having a plurality of holes, electrically connected to the controller, wherein the base is provided with at least one concave portion and at least one first pad disposed in each of the holes separately; and
    an array of tube assemblies, filled with predetermined fluids, detachably disposed in the holes and separately electrically connected to the base, the tube assemblies dispensing the fluids under the control of the controller, wherein the tube assemblies are replaceable;
    wherein each of the tube assemblies further comprises:
    a receptacle, having a passage, provided with at least one protrusion corresponding to the at least one recess for engaging with the base, wherein the receptacle is provided with at least one second pad corresponding to the at least one first pad, and the second pads abut the first pads when the tube assemblies are inserted into the holes of the base;
    a capillary tube, for retaining the fluid, disposed in the receptacle at one end of the passage; and
    a print chip head, disposed in the receptacle at the other end of the passage, abutting the second pads and communicating with the capillary tube.

11. A dispensing device for a biochemical analysis comprising:
    a controller; and
    at least one micro-dispenser, for dispensing a predetermined amount of reagents to a substrate used in the biochemical analysis, electrically connected to the controller, wherein the micro-dispenser comprises:
    a base, having a plurality of holes, electrically connected to the controller; and
    an array of tube assemblies, filled with predetermined reagents, detachably disposed in the holes and separately electrically connected to the base, the tube assemblies dispensing the reagents under the control of the controller when the base faces the substrate, wherein the tube assemblies are replaceable;

wherein each of the tube assemblies further comprises:

a receptacle having a passage;

a capillary tube, for retaining the fluid, disposed in the receptacle at one end of the passage; and a print chip head, disposed in the receptacle at the other end of the passage, communicating with the capillary tube.

12. The dispensing device as claimed in claim 11, wherein the base is provided with at least one recess formed adjacent to each hole, and the receptacle of each of the tube assemblies is provided with at least one protrusion corresponding to the at least one recess for engaging with the base.

13. The dispensing device as claimed in claim 11, wherein each of the tube assemblies is marked with a code for indicating the type of reagent contained therein.

14. The dispensing device as claimed in claim 11, wherein the base is provided with a first detecting device for detecting the amount of the reagent.

15. The dispensing device as claimed in claim 11, wherein each of the tube assemblies is provided with a second detecting device for detecting the amount of the reagent contained therein.

16. The dispensing device as claimed in claim 11, wherein the micro-dispenser is pulse pressure ink-jet type.

17. The dispensing device as claimed in claim 11, wherein the micro-dispenser is bubble jet ink-jet type.

18. The dispensing device as claimed in claim 11, wherein the micro-dispenser is slit jet ink-jet type.

19. A dispensing device for a biochemical analysis comprising:

a controller; and at least one micro-dispenser, for dispensing a predetermined amount of reagents to a substrate used in the biochemical analysis, electrically connected to the controller, wherein the micro-dispenser comprises:

a base, having a plurality of holes, electrically connected to the controller, wherein the base is provided with at least one first pad disposed in each of the holes separately; and an array of tube assemblies, filled with predetermined fluids, detachably disposed in the holes and separately electrically connected to the base, the tube assemblies dispensing the fluids under the control of the controller, wherein the tube assemblies are replaceable;

wherein each of the tube assemblies further comprises:

a receptacle having a passage, wherein the receptacle is provided with at least one second pad corresponding to the at least one first pad, and the second pads abut the first pads when the tube assemblies are inserted into the holes of the base;

a capillary tube, for retaining the fluid, disposed in the receptacle at one end of the passage; and a print chip head, disposed in the receptacle at the other end of the passage, communicating with the capillary tube.

20. A dispensing device for a biochemical analysis comprising:

a controller; and at least one micro-dispenser, for dispensing a predetermined amount of reagents to a substrate used in the biochemical analysis, electrically connected to the controller, wherein the micro-dispenser comprises:

a base, having a plurality of holes, electrically connected to the controller, wherein the base is provided with at least one concave portion and at least one first pad disposed in each of the holes separately; and an array of tube assemblies, filled with predetermined fluids, detachably disposed in the holes and separately electrically connected to the base, the tube assemblies dispensing the fluids under the control of the controller, wherein the tube assemblies are replaceable;

wherein each of the tube assemblies further comprises:

a receptacle, having a passage, provided with at least one protrusion corresponding to the at least one recess for engaging with the base, wherein the receptacle is provided with at least one second pad corresponding to the at least one first pad, and the second pads abut the first pads when the tube assemblies are inserted into the holes of the base;

a capillary tube, for retaining the reagent, disposed in the receptacle at one end of the passage; and a print chip head, disposed in the receptacle at the other end of the passage, abutting the second pads and communicating with the capillary tube.

* * * * *